United States Patent [19]

Merger et al.

[11] Patent Number: 5,162,552
[45] Date of Patent: Nov. 10, 1992

[54] PREPARATION OF 4-ACETALS OF BUTENE-1,4-DIAL AND NOVEL ACETALS OF BUTENE-1,4-DIAL

[75] Inventors: Franz Merger, Frankenthal; Rolf Fischer, Heidelberg; Hans Horler, Darmstadt; Juergen Frank, Schwetzingen, all of Fed. Rep. of Germany

[73] Assignee: BASF Aktiengesellschaft, Ludwigshafen, Fed. Rep. of Germany

[21] Appl. No.: 44,805

[22] Filed: Apr. 30, 1987

[30] Foreign Application Priority Data

May 23, 1986 [DE] Fed. Rep. of Germany ....... 3617409

[51] Int. Cl.$^5$ .................... C07D 319/06; C07C 69/66; C07C 59/147; C07C 45/00
[52] U.S. Cl. .................................. 549/375; 560/174; 562/577; 564/502; 568/461
[58] Field of Search ...................... 549/375; 560/174; 562/577; 564/502; 568/461

[56] References Cited

PUBLICATIONS

March, Advanced Organic Chemistry: Reactions, Medianisms, and Structure, p. 671 (1968).
March, *Advanced Organic Chemistry: Reactions, Mechanisms and Structure* p. 670 (1968).
Beilsteins Handbuch der Organischen Chemie, 1922, vol. 4, p. 54.
Chemische Berichte 93, pp. 1305–1306 (1960).
Angewandte Chemie 88, p. 261 (1976).
J. Heterocyclic Chem. 7, pp. 1153–1155 (1970).
J. Chem. Soc. (C), 1971, pp. 2984–2985.
March, Advanced Organic Chemistry, 1968, pp. 670–671, 692–693.

*Primary Examiner*—John W. Rollins
*Attorney, Agent, or Firm*—John H. Shurtleff

[57] ABSTRACT

A process for the preparation of 4-acetals of butene-1,4-dial of the formula

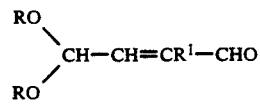

$$\begin{array}{c}\text{RO}\\ \phantom{RO}\diagdown\\ \phantom{RRRR}\text{CH—CH=CR}^1\text{—CHO}\\ \phantom{RO}\diagup\\ \text{RO}\end{array} \qquad \text{I}$$

where R is an alkyl, alkenyl, cycloalkyl or aralkyl radical of 1 to 12 carbon atoms which may contain alkoxy groups, or the two radicals R together form an alkylene or alkenylene radical of 2 to 10 carbon atoms which may contain alkoxy groups, and R$^1$ is an alkyl, alkenyl or alkynyl radical of 1 to 12 carbon atoms which may be substituted by cycloaliphatic, aromatic or heterocyclic radicals or by hydroxyl, ether, thioether, acyl, alkylamino, carboxyl or carbalkoxy groups, or is an unsubstituted or substituted aryl radical or an alkoxy, alkylthio or acyloxy group, wherein a glyoxal monoacetal of the formula

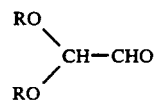

$$\begin{array}{c}\text{RO}\\ \phantom{RO}\diagdown\\ \phantom{RRR}\text{CH—CHO}\\ \phantom{RO}\diagup\\ \text{RO}\end{array} \qquad \text{II}$$

is reacted with an aldehyde of the formula $$\text{R}^1\text{—CH}_2\text{—CHO} \qquad \text{III}$$

at up to 150° C., and novel acetals of butene-1,4-dial.

14 Claims, No Drawings

PREPARATION OF 4-ACETALS OF BUTENE-1,4-DIAL AND NOVEL ACETALS OF BUTENE-1,4-DIAL

The present invention relates to a process for the preparation of 4-acetals of butene-1,4-dial which are substituted in the 2-position, by reacting a glyoxal monoacetal with an aldehyde which has an α-methylene group, and novel acetals of butene-1,4-dial.

4-acetals of 2-methylfumardialdehyde are useful building blocks for the synthesis of terpenes possessing biological and pharmacological activity. Several processes have been proposed for their preparation. For example, German Laid-Open Applications DOS 2,357,752 and DOS 2,357,810 disclose that acetals of 3-methyl-2-butenal can be oxidized with selenium dioxide to give the corresponding 4-acetals of 2-methylfumardialdehyde. German Laid-Open Application DOS 2,225,612 describes a process for the preparation of cyclic 4-acetals of 2-methylfumardialdehyde, in which the corresponding acetals of 3-methyl-4-hydroxy-2-butenal are oxidized with a solution of sulfuric acid and chromic acid.

European Patent 9,752 describes the reaction of cyclic acetals of 3-methyl-3-butenal with nitrosating agents, such as nitrosyl chloride or nitrites, in the presence of methanol and hydrochloric acid. This reaction gives 2-chloro-2-methylbutane-1,4-dial bisacetals, from which hydrogen chloride is eliminated with a base to give bisacetals of 2-methyl-2-butene-1,4-dial, which can be hydrolyzed selectively with dilute aqueous acids to give 4-acetals of 2-methylfumardialdehyde.

All of these processes employ oxidizing agents which are expensive and/or toxic and whose reduction products present disposal problems. This is particularly so in the case of selenium dioxide, chromic acid, nitrosyl chloride and nitrites. If oxygen or oxygen-donating compounds (hydrogen peroxide, percarboxylic acids or organic hydroperoxides) are used as oxidizing agents, expensive safety measures are necessary. Moreover, the required starting compounds are generally only obtainable by multistage syntheses.

In the synthesis described in German Laid-Open Application DOS 2,513,999, glyoxal monoacetals are reacted with Grignard compounds to give acetals of 2-hydroxy-3-butenal, the latter are acetylated to give the corresponding acetals of 2-acetoxy-3-butenal, and hydroformylation is then carried out in the presence of a rhodium compound to give a mixture of acetals of 3- and 4-formyl-2-acetoxybutanal, of which only the 3-formyl compound gives 4-acetals of 2-methylfumardialdehyde after elimination of acetic acid.

We have found that 4-acetals of butene-1,4-dial of the formula

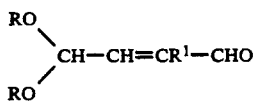

where R is an alkyl, alkenyl, cycloalkyl or aralkyl radical of 1 to 12 carbon atoms which may contain alkoxy groups, or the two radicals R together form an alkylene or alkenylene radical of 2 to 10 carbon atoms which may contain alkoxy groups, and $R^1$ is an alkyl, alkenyl or alkynyl radical of 1 to 12 carbon atoms which may be substituted by cycloaliphatic, aromatic or heterocyclic radicals or by hydroxyl, ether, thioether, acyl, alkylamino, carboxyl or carbalkoxy groups, or is an unsubstituted or substituted aryl radical or an alkoxy, alkylthio or acyloxy group, are particularly advantageously obtained if a glyoxal monoacetal of the formula

where the radicals R have the above meanings, is reacted with an aldehyde of the formula

where $R^1$ has the above meanings, at from 20° to 150° C.

The advantageous result of the novel process, which permits glyoxal monoacetals to be converted to 4-acetals of 2-methylfumardial with propionaldehyde in one reaction step and which furthermore permits other aldehydes possessing α-methylene groups to be converted to 4-acetals of fumardial which are substituted in the 2-position, was not to be expected in view of the technical knowledge mentioned above.

In the glyoxal monoacetals of the formula II, R is, for example, an alkyl, alkenyl, aralkyl or cycloalkyl radical of 1 to 12, preferably 1 to 8, carbon atoms, such as methyl, ethyl, propyl, allyl, butyl, butenyl, isobutyl, methallyl, benzyl, cyclopentyl, cyclohexyl or cyclooctyl. The two radicals R together may furthermore form a straight-chain or branched alkylene radical of 2 to 8, preferably 2 to 5, carbon atoms which may carry alkoxy groups, such as methoxy or ethoxy groups. These are, for example, radicals of the formulae —(CH$_2$)$_2$—, —(CH$_2$)$_3$—, —(CH$_2$)$_4$—, —CH$_2$—C(CH$_3$)$_2$—CH$_2$—, —CH$_2$—CH(CH$_3$)—CH$_2$—, —(CH$_2$)$_2$—CH—(CH$_3$)—CH$_2$—, —CH$_2$—CH(CH$_3$)—, —CH$_2$—C(CH$_3$)(CH$_3$OCH$_2$—CH$_2$)—CH$_2$—, —CH$_2$—CH(OCH$_3$)—CH$_2$— and —CH$_2$—CH(CH$_2$—OCH$_3$)—.

Specific examples are the monoacetals of glyoxal with methanol, ethanol, propanol, allyl alcohol, butanol, isobutanol, methallyl alcohol, methoxyethanol, ethoxyethanol, glycol, 1,2- and 1,3-propylene glycol, butane-1,3-diol, 2-methylpropane-1,3-diol, 2,2-dialkylpropane-1,3-diols, 2-methyl-2-methoxymethylpropane-1,3-diol, ethylmethoxymethylpropane-1,3-diol, butane-1,4-diol, 2-methylbutane-1,4-diol and 2-ethylbutane-1,4-diol. The monoacetal of glyoxal with neopentylglycol, i.e. 2-formyl-5,5-dimethyl-1,3-dioxane, is particularly suitable.

In the aldehydes of the formula III, $R^1$ is, for example, a straight-chain or branched alkyl, alkenyl or alkynyl radical of 1 to 12, preferably 1 to 8, carbon atoms which may contain cycloaliphatic, aromatic or heterocyclic radicals, such as phenyl or pyridyl, and hydroxyl, alkoxy, thioether, acetoxy, alkylamino, carboxyl or carbalkoxy groups. $R^1$ may furthermore be alkoxy or alkylthio, such as methoxy or methylthio, acyloxy or an unsubstituted or substituted aryl radical, such as phenyl, which may contain, for example, alkyl or alkoxy groups or halogen atoms.

Examples of aldehydes of the formula III are propanal, butanal, pentanal, 3-pentenal, 4-pentenal, 3-methylbutanal, phenylacetaldehyde, 3-phenylpropanal, 3-phenylbutanal, 3-anisylpropanal and -butanal, 3-pyridylpropanal, 4-hydroxybutanal, 4-acetoxybutanal, 5-formylvaleric acid, 5-formylvalerates, 4-dimethylaminobutanal, methoxyacetaldehyde, ethoxyacetaldehyde, 3-methylthiopropanal, acetoxyacetaldehyde, 4-methylthiobutanal, 3,6-dioxaheptanal, 3,5-dimethyloct-5-enal, 4-oxapentanal and 4,7-dioxaoctanal.

The acetals of the formula II are reacted with the aldehydes of the formula III at up to 150° C., preferably from 20° to 120° C., in particular from 40° to 100° C. The molar ratio of the starting materials of the formulae III and II is advantageously kept in the range from 1:1 to 2:1, preferably from 1.1:1 to 1.8:1, in particular from 1.2:1 to 1.5:1. However, other molar ratios are also possible.

In a particularly advantageous procedure, the process for the preparation of the 4-acetals of butene-1,4-dial is carried out in the presence of a catalyst which consists of a secondary amine and an acid, preferably a carboxylic acid. Examples of catalysts of the stated type are salts of the dialkylamines dimethylamine, diethylamine, diisopropylamine, dibutylamine, diisobutylamine, methylethylamine, methylbutylamine, ethylbutylamine, methylhydroxyethylamine, pyrrolidine, piperidine and morpholine with a monobasic or polybasic acid, in particular a monocarboxylic or dicarboxylic acid, such as acetic acid, propionic acid, butyric acid, isobutyric acid, valeric acid, isovaleric acid, 2-methylbutyric acid, hexanoic acid, methylpentanoic acid, ethylhexanoic acid, isononanoic acid, methoxyacetic acid, pivalic acid, methoxypivalic acid, oxalic acid, succinic acid, glutaric acid, adipic acid, hydroxybutyric acid, malic acid and hydroxypivalic acid. Where an aldehydic acid, such as 5-formylvaleric acid, is employed, it is not necessary to use an additional carboxylic acid.

Catalysts of this type are described in, for example, EP-B-58 927. In the case of these catalysts, it is not necessary for the amines and the acids to be used in equivalent proportions. The amount of the catalyst used for the reaction can likewise be varied within wide limits. Advantageously, the catalyst is used in an amount of from 1 to 150, preferably from 5 to 100, in particular from 20 to 100, mol %, based on the starting material of the formula II. If, in order to achieve a rapid reaction under mild conditions, more than negligible catalytic amounts of catalyst (e.g. more than 5 mol % based on II) are used, the catalyst is recovered after isolation of the product, for example by phase separation, extraction or distillation, and is used repeatedly, so that a low overall consumption results.

In the novel process, the 4-acetals of butene-1,4-dial are obtained from economical basic building blocks by a procedure which is simple to carry out in terms of process engineering. For example, the novel process permits the preparation of the 4-neopentylglycol acetal of methylfumardialdehyde by reacting, according to the invention, 2-formyl-5,5-dimethyl-1,3-dioxane with propionaldehyde according to the equation:

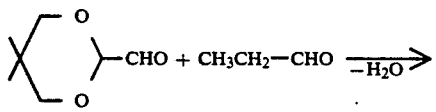

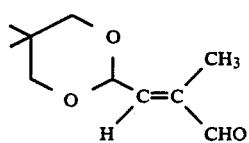

The high efficiency of the novel process was particularly surprising. The desired compounds of the formula I are obtained in high yields and with high trans selectivity. Surprisingly, a large number of potential competing reactions are of little or no importance. Thus, predominantly or exclusively autoaldolization and autocondensation of the starting compounds II and II and coaldolization were to be expected.

The result of the novel reaction is all the more surprising since the reaction of glyoxal monoacetal with acetaldehyde does not give the corresponding 4-acetal of fumaraldehyde but fairly high molecular weight products of acetaldehyde.

The present invention furthermore relates to the novel acetals of butene-1,4-dial of the formula

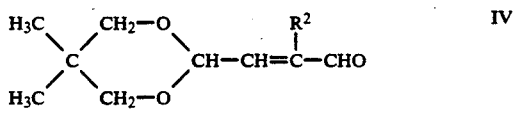

where $R^2$ is an alkyl, alkenyl or alkynyl radical of 2 to 8 carbon atoms which may contain phenyl, pyridyl, hydroxyl, alkoxy, thioether, acetoxy, alkylamino, carboxyl or carbalkoxy, or is alkoxy, alkylthio or acyloxy or a phenyl radical which may be substituted by alkyl, alkoxy or halogen.

These novel acetals are intermediates for the preparation of active ingredients.

EXAMPLE 1

A mixture of 90 g of dimethylamine in 135 g of water and 120 g of acetic acid is heated to 50° C., a solution of 232 g of propionaldehyde in 288 g of 2-formyl-5,5-dimethyl-1,3-dioxane is run in at this temperature in the course of one hour, while cooling and stirring, the temperature is then increased to 80° C. and the reaction mixture is stirred for a further hour. After the mixture has cooled to room temperature, the aqueous catalyst solution (lower phase) is separated off and the organic phase is subjected to fractional distillation to give 298 g of 4-neopentylglycol acetal of 2-methylfumardialdehyde (2-(2-formylpropenyl)-5,5-dimethyl-1,3-dioxane) of boiling point 68°-71° C./ 2 mbar, corresponding to 81% of theory, based on 2-formyl-5,5-dimethyl-1,3-dioxane, as well as 104 g of 2-methylpentenal (bp. 30°-40° C./30 mbar).

EXAMPLE 2

504 g of a solution of 240 g of propionaldehyde in 264 g of diethoxyacetaldehyde (glyoxal(mono)diethylacetal) are run into a mixture of 48 g of dimethylamine in 72 g of water and 80 g of propionic acid at 40° C. in the course of 30 minutes, while stirring. The reaction mixture is then stirred for a further 3 hours. After the lower aqueous phase has been separated off, fractional distillation of the organic phase gives 237 g (68.9% of theory) of 2-methyl-4,4-diethoxybut-2-enal of boiling point 67°-69° C./8 mbar.

EXAMPLE 3

A solution of 163 g of propionaldehyde in 288 g of 2-formyl-5,5-dimethyl-1,3-dioxane is run into a mixture of 90 g of dimethylamine in 135 g of water and 120 g of acetic acid at 80° C. in the course of 30 minutes, while cooling and stirring. The reaction mixture is then stirred for a further hour at the same temperature. After the lower aqueous phase has been separated off, fractional distillation of the organic phase gives a fraction of 40 g of methylpentenal (bp. 34°-38° C./30 mbar; 20%, based on propionaldehyde) and 328 g (89.1% of theory) of 4-neopentylglycol acetal of 2-methylfumardialdehyde of boiling point 70°-72° C./2 mbar, and a fraction of 18 g (4.45% of theory) of 2-(1-hydroxy-2-formylpropyl)-5,5-dimethyldioxane(aldol).

EXAMPLE 4

A solution of 116 g of propionaldehyde in 288 g of 2-formyl-5,5-dimethyl-1,3-dioxane is reacted as described in Example 3 to give 356 g of an organic phase which, according to gas chromatographic analysis, contains the following: 3.1% by weight of methylpentenal, 2.7% by weight of 2-formyl-5,5-dimethyl-1,3-dioxane, 5.8% by weight of 2-(1-hydroxy-2-formylpropyl)-5,5-dimethyl-1,3-dioxane and 86.8% by weight of 4-neopentylglycol acetal of 2-methylfumardialdehyde, corresponding to 84% of theory.

EXAMPLE 5

A solution of 288 g of n-butyraldehyde in 288 g of 2-formyl-5,5-dimethyl-1,3-dioxane is reacted as described in Example 3, and 285.6 g (72.1% of theory) of 4-neopentylglycol acetal of 2-ethylfumardialdehyde of boiling point 82°-84° C./1 mbar are obtained by fractional distillation, in addition to 128 g of 2-ethylhexenal as light ends.

EXAMPLE 6

A solution of 300 g of phenylacetaldehyde in 288 g of 2-formyl-5,5-dimethyl-1,3-dioxane is reacted as described in Example 3, and 331 g (67.2% of theory) of 4-neopentylglycol acetal of 2-phenylfumardialdehyde with a boiling point of from 124° to 126° C./1 mbar are obtained by fractional distillation.

EXAMPLE 7

A solution of 415 g of 3-phenylbutanal in 288 g of 2-formyl-5,5-dimethyl-1,3-dioxane is reacted as described in Example 3, and 490 g (65.5% of theory) of 4-neopentylglycol acetals of 2-(1-phenylethyl)-but-2-ene-1,4-dial (E:Z=2:1) of boiling point 160°-162° C./1 mbar are obtained by fractional distillation.

EXAMPLE 8

A mixture of 129 g of dibutylamine and 74 g of propionic acid is heated to 60° C., and a mixture of 144 g of 2-formyl-5,5-dimethyl-1,3-dioxane and 144 g of methyl 5-formylvalerate is run in at this temperature in the course of 30 minutes, while stirring and cooling. Stirring is continued for a further two hours, the mixture is cooled to room temperature, 400 ml of water are added while stirring, and the organic phase is separated off and washed with 3 times 150 ml of water. Fractional distillation gives 172.3 g (63.8% of theory) of 4-neopentylglycol acetal of 2-(3-methoxycarbonyl)-propylbut-2-ene-1,4-dial (E:Z=20:1) of boiling range 148°-154° C./2 mbar.

We claim:

1. A process for the preparation of a 4-acetal of butene-1,4-dial of the formula

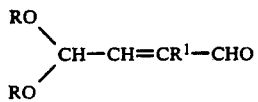

I where R is an alkyl, alkenyl, cycloalkyl or aralkyl radical of 1 to 12 carbon atoms which may contain alkoxy groups, or the two radicals R together form an alkylene or alkenylene radical of 2 to 10 carbon atoms which may contain alkoxy groups, and $R^1$ is an alkyl, alkenyl or alkynyl radical of 1 to 12 carbon atoms which may be substituted by cycloaliphatic, aromatic or heterocyclic radicals or by hydroxy, ether, thioether, acyl, alkylamino, carboxyl or carbalkoxy groups, or is an unsubstituted or substituted aryl radical or an alkoxy, alkylthio or acyloxy group which process comprises:

reacting a glyoxal monoacetal of the formula

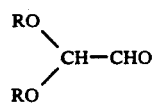

II where R has the above meanings, with an aldehyde of the formula

III where $R^1$ has the above meanings, at from 20° C. to 150° C. and in the presence of a catalyst consisting essentially of a secondary amine and an acid.

2. A process as claimed in claim 1, wherein the acid used is a carboxylic acid.

3. A process as claimed in claim 1, wherein the reaction is carried out at a temperature of from 40° to 100° C.

4. A process as claimed in claim 1, wherein the molar ratio of the aldehyde (III) to the glyoxal monoacetal (II) is kept in the range from 1:1 to 2:1.

5. A process as claimed in claim 1, wherein the molar ratio of the aldehyde (III) to the glyoxal monoacetal (II) is kept in the range from 1.1:1 to 1.8:1.

6. A process as claimed in claim 1, wherein the molar ratio of the aldehyde (III) to the glyoxal monoacetal (II) is kept in the range from 1.2:1 to 1.5:1.

7. A process as claimed in claim 1, wherein the reaction is carried out in the presence of a catalyst consisting essentially of a salt of a secondary amine and a carboxylic acid.

8. A process as claimed in claim 7, wherein the secondary amine is selected from the group consisting of dimethylamine, diethylamine, diisopropylamine, dibutylamine, diisobutylamine, methylethylamine, methylbutylamine, ethylbutylamine, methylhydroxyethylamine, pyrrolidine, piperidine and morpholine, and the carboxylic acid is selected from the group consisting of acetic acid, propionic acid, butyric acid, isobutyric acid, valeric acid, isovaleric acid, 2-methylbutyric acid, hexanoic acid, methylpentanoic acid, ethylhexanoic acid, isononanoic acid, methoxyacetic acid, pivalic acid, methoxypivalic acid, oxalic acid, succinic acid, glutaric acid, adipic acid, hydroxybutyric acid, malic acid and hydroxypivalic acid.

9. A process as claimed in claim 7, wherein the catalyst is used in an amount of from 1 to 150 mol %, based on the glyoxal monoacetal (II) as a starting material.

10. A process as claimed in claim 7, wherein the reaction is carried out at a temperature of from 40° to 100° C.

11. A process as claimed in claim 7, wherein 5-formylvaleric acid is used both as a starting material and as an acid for the catalyst.

12. A process as claimed in claim 7, wherein the amine is dimethylamine and the acid is acetic acid.

13. A process as claimed in claim 7, wherein the amine is dimethylamine and the acid is propionic acid.

14. A process as claimed in claim 7, wherein the amine is dibutylamine and the acid is propionic acid.

* * * * *